United States Patent
Rauth et al.

(12)

(10) Patent No.: US 7,022,835 B1
(45) Date of Patent: Apr. 4, 2006

(54) METHOD FOR BINDING NUCLEIC ACIDS TO A SOLID PHASE

(75) Inventors: Holger Rauth, Berlin (DE); Richard Reinhardt, Berlin (DE); Eckard Nordhoff, Berlin (DE)

(73) Assignee: Max-Planck-Gesellschaft zur Foerderung der Wissenschaften. E.V., Munich (DE)

( * ) Notice: Subject to any disclaimer, the term of this patent is extended or adjusted under 35 U.S.C. 154(b) by 0 days.

(21) Appl. No.: 10/069,974

(22) PCT Filed: Sep. 8, 2000

(86) PCT No.: PCT/EP00/08807

§ 371 (c)(1),
(2), (4) Date: Jul. 9, 2002

(87) PCT Pub. No.: WO01/19980

PCT Pub. Date: Mar. 22, 2001

(30) Foreign Application Priority Data

Sep. 10, 1999 (DE) ................................ 199 43 374

(51) Int. Cl.
*C07H 21/00* (2006.01)
*C07H 21/02* (2006.01)
*C07H 21/04* (2006.01)
*C07H 19/00* (2006.01)

(52) U.S. Cl. ................. 536/25.4; 536/25.3; 536/25.41; 536/26.73; 536/27.12

(58) Field of Classification Search ............... 536/25.3, 536/25.4, 26.73, 27.12, 25.41
See application file for complete search history.

(56) References Cited

U.S. PATENT DOCUMENTS

| 4,579,661 A | | 4/1986 | Hedman et al. |
| 5,668,268 A | * | 9/1997 | Tang et al. ................. 536/25.3 |
| 5,705,628 A | * | 1/1998 | Hawkins ..................... 536/25.4 |

FOREIGN PATENT DOCUMENTS

| EP | 0389063 A | 9/1990 |
| EP | 0580305 A | 1/1994 |

* cited by examiner

*Primary Examiner*—James O. Wilson
*Assistant Examiner*—Traviss C. McIntosh, III
(74) *Attorney, Agent, or Firm*—Rothwell, Figg, Ernst & Manbeck, P.C.

(57) ABSTRACT

The invention concerns a method for binding nucleic acids to a solid phase in which a nucleic acid containing solution is contacted with a solid phase which has hydrophobic and hydrophilic groups on its surface or/and which comprises a hydrophilic, water-containing polymer matrix, in the presence of dehydrating reagents, in particular in the presence of a salt and polyethylene glycol whereby the nucleic acid is bound to the surface.

27 Claims, 3 Drawing Sheets

METHOD FOR BINDING NUCLEIC ACIDS TO A SOLID PHASE

The invention concerns methods for binding and immobilizing nucleic acids, respectively, on a solid phase and for purifying the bound nucleic acids in which the solid phase is coated with hydrophilic and hydrophobic groups or/and a hydrophilic water-containing polymer matrix.

For many working techniques it is necessary that the nucleic acids that are used and in particular the DNA is free from interfering accompanying substances. Hence nucleic acids obtained by conventional methods have to be purified in most cases before further use. For example undesired byproducts, excess primers, non-incorporated nucleotides and salts of the reaction buffer have to be separated before sequencing PCR (polymerase chain reaction) products since they could interfere with the sequencing reaction. Also in the case of DNA amplification with the aid of cells, a purification is necessary in which the cell debris after a lysis is separated, before the desired DNA is processed further. The desired DNA then has to be freed from impurities such as RNA, proteins, salts etc. before use e.g. for a restriction digestion or a sequencing reaction. An initial purification is also required for a quantitative determination of nucleic acids for example by means of UV absorption measurements since the nucleic acid solution has to be free of other components that absorb in the same wavelength range as the desired products such as RNA, primers, nucleotides etc. to ensure an accurate determination. Purified nucleic acids also have to be used for a concentration determination by fluorimetric measurements to prevent unspecific fluorescence from falsifying the result. In the case of mass spectrometric investigations of nucleic acids, in particular DNA, for example using MALDI-MS (matrix assisted laser desorption/ionization mass spectrometry) it is necessary that the sample molecules are substantially free from accompanying substances such as buffer substances, metal cations, excess primers, peptides, lipids, detergents etc. which could interfere with the analysis. Furthermore the nucleic acid is advantageously converted into the ammonium form in order to carry out a MALDI-MS analysis. In this manner discrete analyte signals and a good signal-to-noise ratio are achieved and discrimination of the sample signal by accompanying substances is prevented.

When processing a few samples it is possible to use laborious manual techniques for the purification. However, in order to cope with a large number of samples it is necessary to provide a suitable, technically simple and cost-effective purification process that can be automated in order to manage the required throughput.

Various methods for purifying nucleic acids are known. Various techniques are used for purification by means of columns. For example in the case of the QIAquickPCR purification kit from Qiagen, DNA is adsorbed to a silica membrane with the aid of a special binding buffer. The effect of the binding buffer is that only DNA of a certain length is adsorbed and excess primers and nucleotides can be separated. After washing the DNA, it is then eluted from the column with a suitable elution agent.

In the case of exclusion chromatography a liquid phase which contains dissolved DNA is applied to a gel matrix and the macromolecules penetrate into the network of the matrix to different depths depending on their size. Smaller molecules penetrate more deeply than larger molecules and are thus retained for a longer period on the column. Molecules which are larger than the largest pores of the swollen gel matrix used cannot penetrate into the gel particles and thus migrate past them and are the first to leave the column. A purification can be carried out based on the different size of the desired DNA on the one hand and on the primers and nucleotides on the other hand. Sephacryl from Pharmacia is a frequently used material for the gel matrix.

In the column techniques the eluate is usually obtained by centrifugation which is why it is very complicated to automate these techniques. Hence column procedures are not suitable for a high sample throughput. Moreover purification by means of columns requires complex apparatus and is hence very costly.

Another method for purifying DNA is preparative isolation by means of gel electrophoresis. In this method the molecules are separated according to their size. The desired band containing the molecules of interest is cut out and then directly eluted from the gel. This method is also difficult to automate, the limiting step being cutting out the desired bands. Hence it has previously only been possible to use this method for manual applications.

Another method for purifying nucleic acids is magnetic separation by specifically binding the nucleic acids to a functionalized surface. Only certain DNA fragments are bound to particles in the specific binding process by means of high affinity interactions or covalent binding. For example biotinylated products are bound by means of high affinity interactions to magnetic particles coated with immobilized streptavidin. In addition to the use of surfaces which carry one partner of a specific binding pair, it is also possible to use particles which carry a primer on their surface. Then only fragments which have a sequence that is complementary to this primer are bound under suitable hybridization conditions. However, these methods require a laborious preparation of the solid phases as well as of the molecules to be purified for example by derivatization and are thus limited to molecules prepared in this manner.

WO 94/11103 describes such a method using magnetizable polymer particles which carry specific affinity ligands on their surface.

EP 0 885 958 describes a method for isolating DNA using at least two different magnetic particles which carry partners of a specific binding pair such as probes, biotin or streptavidin.

U.S. Pat. No. 5,405,951 describes a method in which DNA is bound to silica surfaces using chaotropic salts. However, chaotropic salts are injurious to health. Moreover the method described in the U.S. Pat. No. 5,405,951 requires work at an elevated temperature.

U.S. Pat. No. 5,705,628 describes a method in which DNA is bound to magnetic microparticles which have a surface provided with carboxyl groups using a binding buffer. However, due to the low yield it is necessary to use a relatively large number of particles per sample and the carboxyl group modification only allows the use of a few special types of particles.

Hence the object of the invention was to provide a method for immobilizing/binding and purifying nucleic acids, respectively, which at least partially avoids the disadvantages of the methods known in the prior art and which in particular enables a simple and cost-efficient purification of a large number of samples.

This object is achieved according to the invention by a method for binding nucleic acids to a solid phase which is characterized in that a solution containing nucleic acids is contacted with a solid phase which has hydrophobic and hydrophilic groups on its surface in the presence of a salt and polyethylene glycol, whereby the nucleic acids are bound to the surface. Under these conditions the nucleic acid molecules bind to the said surface and are hence ready for solid phase-assisted washing processes during which interfering substances can be effectively separated and if required the sample molecules can be converted into the ammonium form advantageous for mass spectrometry.

The method according to the invention enables nucleic acids to be isolated from solutions, the term nucleic acid being also understood to include salts thereof. The binding of the nucleic acids to the surface of the solid phase preferably takes place reversibly and unspecifically and is therefore not limited by special high affinity binding pairs such as streptavidin/avidin or to nucleic acids with certain sequence sections which can for example be bound to the surfaces by hybridization. According to the invention the nucleic acids are bound independently of their sequence and thus a universal binding matrix for nucleic acids is obtained. The method is technically simple to carry out and can be readily automated to enable a high sample throughput at low costs. The immobilization and also the elution of the nucleic acids from the surface can be carried out at room temperature. Furthermore it was surprisingly found that nucleic acids can be bound in a high yield to the said surfaces. As a consequence fewer particles per sample have to be used for the method according to the invention compared to the known methods which results in further simplification and cost reduction.

The part of the solid phase used that is brought into contact with the solution preferably has a proportion of $\geq 1\%$, in particular $\geq 5\%$, preferably $\geq 10\%$ and of $\leq 90\%$, in particular $\leq 50\%$ and preferably $\leq 30\%$ hydrophobic chemical surface groups. In this connection it should be noted that when the percentage of hydrophobic surface groups exceeds a particular value, which can be readily determined by a person skilled in the art for the respective solid phase, an agglomeration of solid phase particles occurs in aqueous solution with the consequence that the solid phase can no longer be resuspended.

Small and in particular magnetic particles are preferably used according to the invention which carry functional hydrophobic groups on their surface such as alkyl or aryl groups to which nucleic acids can be bound unspecifically and reversibly. It is advantageous to use the functional groups known from reverse phase chromatography since their immobilization and handling is well understood and established.

It is also possible to use a solid phase with several active surface regions that are delimited by inert areas in order to provide several spatially delimited reagent fields.

If not already present, the said surface of the solid phase can be prepared by derivatization or by coating. This procedure has the advantage that the material for the solid phase can be chosen freely. The hydrophobic chemical groups are preferably organic groups containing hydrocarbons and can have cyclic, linear or/and branched structures. The surface preferably carries $C_1$–$C_{30}$ alkyl groups or $C_5$–$C_{30}$ aryl groups in particular $C_6$–$C_{24}$ alkyl groups as functional hydrophobic groups. The alkyl groups are particularly preferably selected from $C_8$ alkyl, $C_{18}$ alkyl and mixtures thereof, octadecyl ligands being most preferred.

In addition to hydrophobic groups, the surface also has hydrophilic chemical groups e.g. hydroxyl or/and oxide groups which can optionally be already present in the case of the pre- or/and intermediate coatings mentioned below. As described above small particles with an entirely hydrophobic surface have a particular tendency to agglomerate in aqueous solutions. This problem can be avoided by providing the functional hydrophobic groups also with hydrophilic groups in particular hydroxyl residues. The hydroxyl groups can comprise inorganic hydroxyl groups e.g. silicic acid groups or/and organic hydroxyl groups e.g. monosaccharides or polysaccharides such as agarose. Other suitable hydrophilic groups comprise carbonyl, carboxyl, ester, amino, thiol, sulfate, sulfonyl and similar groups and combinations of such groups. Polyol derivatives such as polyalkylene glycol derivatives can also be used as hydrophilic groups.

The arrangement and the ratio of hydrophobic to hydrophilic groups in the region of the surface intended for nucleic acid binding is adjusted such that the respective particles just no longer agglomerate in aqueous solution but nucleic acid binding is still effective. The functional groups as well as their arrangement can be selected by a person skilled in the art to match the respective parameters such as particle size, particle density, the analyte etc. It is for example possible to apply the hydrophilic groups to separate microregions that are delimited by the hydrophobic groups. However, a "mixed surface" is preferred in which the hydrophobic and hydrophilic groups are next to one another. The hydrophilic groups can also be introduced by means of suitable substituted organic molecules e.g. hydroxy-substituted alkyls. An example of a preferred mixed surface is an alkyl/OH surface in particular a $C_{18}$ alkyl/OH surface.

The said surfaces can be applied directly to the solid phase or by means of a pre- or intermediate coating. Suitable precoatings are for example a polysilicic acid matrix or/and a monosaccharide matrix. Other suitable precoatings are partners of a specific binding pair, for example streptavidin/avidin, on which the actual active layer is then applied. The binding of the hydrophobic or/and hydrophilic groups to the solid phase or the binding of the hydrophobic or/and hydrophilic coating to the precoating and the binding of the precoating to the solid phase can for example be achieved covalently e.g. by esterification, adsorptively or by means of high affinity interactions. In a particularly preferred embodiment a precoating composed of polysilicic acid and monosaccharide is applied to a solid phase such as γ-iron oxide particles with a diameter in the nanometer or micrometer range. This precoating is then provided with hydrophobic groups in particular alkyl groups and optionally also with hydrophilic groups. Particularly good results were obtained with particles which have 10 to 15% alkyl groups, in particular octadecyl groups per silicic acid matrix (mol/mol) and 0.2% octadecyl groups per monosaccharide unit (mol/mol).

Any solid phase known to a person skilled in the art can be used as the solid phase such as microtitre plates, vessels such as Eppendorf vessels, Greiner tubes, Nunc tubes etc. Solid particles having a diameter of $\geq 1$ nm to $\leq 1$ mm are preferably used as the solid phase which enables access to a favourable specific surface per gram particles. The method according to the invention allows the use of different solid phase materials. Preferred solid phase materials are silica, a plastic such as polystyrene or a magnetic or magnetizable material and in particular γ-iron oxide.

Further advantages are gained by using a magnetic solid phase. A magnetic separation is relatively easy to carry out and can be readily automated. If paramagnetic or para- and ferromagnetic particles are used as the solid phase, it is also possible to further reduce agglomeration of the solid particles. Small magnetic particles having a diameter in the nm or μm range are usually used for magnetic particle techniques (e.g. from the Dynal Company, Oslo, Norway) for which the problem of agglomeration is particularly severe. However, the purification according to the invention can also be carried out without agglomeration since an adequate number of hydrophilic groups and in particular hydroxyl groups are provided for the hydrophobic groups.

The binding of nucleic acids or salts thereof to the said surface is mediated according to the invention by a binding buffer. This binding buffer contains a salt and poly-ethylene glycol. An alkaline, alkaline earth or/and ammonium salt which contains in particular a Li, Na, K, Rb, Cs, Fr, Be, Mg, Ca, Sr, Ba, Ra or/and $NH_4$ ion as the cation is preferably used as the salt. The salt used according to the invention preferably contains a halide anion as the anion and in particular a chloride anion. The poly-ethylene glycol (PEG) used preferably has an average molar mass of 1000 to 20000 g/mol, especially of 6000 to 15000 g/mol.

Since the viscosity increases with increasing amounts of PEG, it is preferable to add an alcohol to the binding buffer, in particular methanol, ethanol, propanol and/or butanol and particularly preferably ethanol or/and 2-propanol. The alcohol content of the binding buffer can be up to 50% by weight, preferably 30 to 40% by weight.

In general the salt is preferably used at a concentration of $\leq 5$ mmol/l, in particular of 5 mmol/l to 4 mol/l in particular of up to 3 mol/l and the polyethylene glycol is preferably used at a concentration of 5 to 40% for the method according to the invention. The stated concentrations of salt and PEG are final concentrations and relate to the binding conditions i.e. to the final mixture which contains the sample and a binding buffer and optionally other diluents such as water.

The method according to the invention enables DNA to be immobilized and purified over a wide range of molecular weights. It is also possible to purify single-stranded DNA of only a few bases in size and also double-stranded DNA of several 100 kb in size, in particular BACs, PACs and such like.

Nucleic acids which can be purified by the method according to the invention comprise for example single-stranded DNA, double-stranded DNA, RNA, LNA and nucleic acid-protein, nucleic acid-PNA and nucleic acid-sugar aducts or complexes. It is preferred to immobilize nucleic acids that are amplification products, for example from a PCR reaction or which have been obtained by amplification with the aid of cells e.g. by means of an overnight culture or sequencing reaction products, primer extension reaction products, ligase chain reaction products, restriction endonuclease digestion products etc. However, it is also possible to bind synthetic nucleic acids.

The selective binding of the single-stranded and double-stranded nucleic acids to the said surface can be adjusted on the basis of the concentration of the components and in particular of salt and PEG. It is possible to achieve a selectivity of $\geq 70\%$, in particular of $\geq 80\%$ and particularly preferably of $\geq 90\%$. Double-stranded nucleic acids of $\geq 80$ bp bind selectively also in the presence of single-stranded nucleic acids at a concentration of monovalent cations of 0.5 to 4 mol/l, divalent cations of $\leq 5$ mmol/l and PEG of $\leq 15\%$ by weight. Single-stranded nucleic acids can be bound by adjusting the concentration of divalent cations to >5 mmol/l and <100 mmol/l and PEG to 10 to 30% by weight. The combination of both methods allows the selective purification of ss and ds nucleic acids. Double-stranded nucleic acids can also be fractionated according to size by adjusting the salt and PEG concentrations within the aforementioned ranges. In the case of small nucleic acids, in particular DNA, it has proven to be advantageous to use a final combination of PEG of 15–40% (weight/weight) and a salt content of 10 to 1000 mmol/l.

In another embodiment the invention concerns a method for isolating or/and purifying nucleic acids comprising the steps (a) providing a solution containing nucleic acids,
(b) contacting the solution containing nucleic acids with a solid phase which has hydrophobic and hydrophilic groups on its surface in the presence of a salt and polyethylene glycol whereby the nucleic acid is bound to the surface
(c) separating the solid phase from the solution and
(d) optionally detaching the nucleic acid from the solid phase.

In the case of the preferred use of a magnetic solid phase, it is possible to magnetically separate the solid phase from the solution which thus can be readily automated.

The solid phase is preferably washed once before use. Depending on the application and surface, it is for example possible to use the binding buffer (BP) diluted with water (preferably 1:1) for washing. A solution of 0.5 mol/l EDTA pH 8–9 can also be used. If it is intended to subsequently analyse the sample, it may be appropriate to wash the solid phase with several buffers which may also include an ammonium acetate buffer.

The purification can be further improved by washing the separated solid phase on the surface of which the nucleic acid is bound with a buffer solution which detaches impurities bound to the solid phase but not the nucleic acid bound to the solid phase. The composition of the washing solution is selected in accordance with the application and the surface. Suitable as washing solution are for example 50–70% (vol/vol) ethanol or 2-propanol optionally containing EDTA, CDTA and TRIS in millimolar concentrations as additives. If the sample is subsequently to be analysed using mass spectrometry, it is preferable to use a washing solution containing ammonium acetate in at least one washing step e.g. 0.05 to 5 mol/l ammonium acetate in 60 to 80% ethanol. It is often also advantageous to carry out the purification in several washing steps with different washing buffers.

The nucleic acid molecules or salts thereof bound to the said surface are preferably separated by means of an elution solution, and any liquid can be used as the elution solution which detaches the nucleic acid from the solid-phase. The choice of elution solution depends on the type of surface and analyte and on the subsequent use of the analyte. The following are preferably used as the elution solution: twice distilled water, pH 7 to 8, an aqueous TRIS solution with a TRIS concentration of 1 to 100 mmol/l, preferably with a pH value of 7 to 9, a formamide solution, a loading buffer for electrophoresis, a matrix solution e.g. 3-hydroxypicolinic acid in water (1–200 mmol/l) for MALDI-MS etc.

A magnetic solid phase can in turn be separated by magnetic means after detachment of the nucleic acid which allows a complete automation of the method according to the invention.

The nucleic acids that have been isolated or/and purified by the method according to the invention can be used directly for further analysis e.g. a mass spectrometric (MS) analysis. The complicated manual purification of the prior art by means of columns is not necessary. In contrast it is possible to automatically purify a large number of samples in a cost-effective and rapid manner for an MS analysis, in particular a MALDI-MS analysis or an ESI (electrospray ionisation) MS analysis. This process removes especially accompanying substances such as buffer substances, metal cations, excess primer, peptides, lipids, detergents and such like. The nucleic acid is advantageously converted into the ammonium form in order to carry out a MALDI-MS analysis e.g. by exchanging the ion Na$^+$ for NH$_4^+$ which can be carried out while the nucleic acids are bound to the surface. Hence the type of binding according to the invention allows a purification procedure i.e. the nucleic acid is present in an accessible form and not as a precipitate. Small DNA molecules are of particular interest for an analysis using MALDI-MS. The method according to the invention allows the purification of small DNA molecules above a minimum size of ca. 5 nucleotides and in particular of ≧10 nucleotides. The method according to the invention effectively separates components which would interfere with the MALDI-MS analysis such as buffer substances and metal cations and excess primers that may be present. Moreover the DNA molecules are converted into the ammonium form which is compatible for a MALDI-MS analysis and can be optionally eluted in pure water or in an aqueous matrix solution and thus be directly transferred onto the MALDI target. A modification of the composition of the binding and washing buffer and the sequential use of particles also allows larger DNA molecules to be excluded from the purification which enables a predetermined molecular weight range to be selected e.g. ≧60 bp and ≦100 bp.

Variation of the salt and PEG concentration also enables the efficient purification of small oligonucleotides such as primers (ssDNA) and primer extension products for an analysis with MALDI-MS.

A further advantage is the broad volume range in which the method according to the invention can be used. Volumes in the ml to the upper nl range are possible in particular of <10 ml, preferably <1 ml and especially preferably <100 μl and ≧100 nl, preferably ≧1 μl. The volume range can be adjusted to the respective application, a concentrated sample being obtained in the case of a small volume.

It is also possible to sequence nucleic acids bound according to the invention by known methods. The sequencing conditions of known methods often represent elution conditions i.e. the nucleic acid is not bound to the solid phase during the actual sequencing. In such a case it is advantageous for the purification of the sequencing products to readjust the conditions for binding especially by adding suitable buffers after completion of the sequencing reaction. The solid phase and in particular the beads do not have to be separated for the sequencing reaction and subsequent purification. It has turned out that solid phases and in particular particles often do not survive the thermocycling used for sequencing in an undamaged form. In such a case, new, unused beads are added after the sequencing reaction.

The invention also encompasses a method for synthesizing nucleic acids in which nucleic acids bound according to the invention are extended by at least 1 nucleotide by known methods. An example of such a reaction is the so-called primer extension reaction i.e. the extension of a primer (ssDNA) by at least 1 nucleotide. The extension can be carried out while the nucleic acid is bound to the solid phase. Since, however, the conditions which are set for extending nucleic acids often correspond to elution conditions, the extension can also in this case take place while the nucleic acid is not bound to the solid phase and the extended nucleic acid is then subsequently bound again by adjusting conditions for binding after the extension reaction for example by adding buffer. The solid phase does not have to be separated during the entire reaction.

The nucleic acids immobilized by the method according to the invention can also be used to selectively bind other molecules to be detected such as nucleic acids or DNA binding proteins and can therefore be used in corresponding assays. Hence the invention also comprises a method for detecting an analyte in a sample in which a solution containing nucleic acids is contacted with a solid phase which has hydrophobic and hydrophilic chemical groups in the presence of a salt and polyethylene glycol whereby the nucleic acids are bound to the surface, subsequently the solid phase having the bound nucleic acid is contacted with the sample and the analyte is detected by means of the binding to the bound nucleic acid molecule.

Finally the invention also encompasses a reagent kit for carrying out the method according to the invention which has a binding buffer containing a salt and polyethylene glycol and a solid phase which has hydrophobic and hydrophilic groups on its surface. Such a reagent kit preferably additionally contains washing and elution buffers.

The invention additionally provides a method for binding nucleic acids to a solid phase which is characterized in that a solution containing nucleic acids is contacted with a solid phase which comprises a hydrophilic water-containing polymer matrix in the presence of dehydrating reagents whereby the nucleic acids are reversibly and sequence-unspecifically bound to the solid phase.

It was surprisingly found that the use of hydrophilic water-containing polymer matrices enables a high binding capacity to be obtained with regard to nucleic acids and also enables the isolation of very small DNA fragments, for example having a length of 10 to 100 bp, in particular of 30 to 70 bp. Moreover, depending on the choice of the hydrophilic water-containing polymer matrix, it is possible to selectively bind nucleic acids according to size.

In the method according to the invention the hydrophilic water-containing polymer matrix is preferably firstly contacted with a solution containing nucleic acids and then a dehydrating agent is added in a second step. Suitable dehydrating agents are salts, in particular chaotropic salt buffers at a high concentration and polyethylene glycol. Preferred salts and polyethylene glycols and their concentrations are as described above.

The use of a hydrophilic water-containing polymer matrix as a solid phase material instead of silica or boron silicate glass that is usually used, allows a reversible and sequence-unspecific binding of nucleic acids. The polymer matrix preferably contains 1 to 90, more preferably 10 to 50% by weight water.

The hydrophilic water-containing polymer matrix preferably contains a hydrophilic water-soluble polymer and in particular a hydrophilic water-soluble organic polymer. Polysaccharides are particularly suitable and in particular polysaccharides with terminal hydroxyl groups such as dextran or starch. Dextran is particularly preferred. The hydrophilic water-containing polymer matrix is particularly preferably provided as an envelope polymer around a magnetic core for example in the form of dextran magnetite particles.

The surface of the hydrophilic water-containing polymer matrix can contain hydrophilic or/and hydrophobic groups. An embodiment is preferred in which a solid phase is used which has hydrophobic as well as hydrophilic groups on its surface as described above and at the same time comprises a hydrophilic water-containing polymer matrix.

A solid phase with a hydrophilic water-containing polymer matrix can be used in the same manner as described above in a method for isolating or/and purifying nucleic acids or in a method for detecting an analyte in a sample. Furthermore it can be used to determine the nucleic acid sequence of a nucleic acid or to synthesize nucleic acids.

The method according to the invention is further illustrated by the attached figures and the following examples.

FIG. 1 (comprising FIGS. 1a and 1b) shows an agarose gel of PCR products purified according to the invention and of PCR products that have been purified using COOH-coated particles:

FIG. 2a shows the MALDI time-of-flight mass spectrum of PCR products purified according to the invention having 47 or 48 base pairs.

FIG. 2b shows the MALDI time-of-flight mass spectrum of a PCR product purified according to the invention having 80 bp.

FIG. 2c shows the MALDI time-of-flight mass spectrum of a DNA single-strand purified according to the invention of 24 nucleotides in length.

Figure 2:
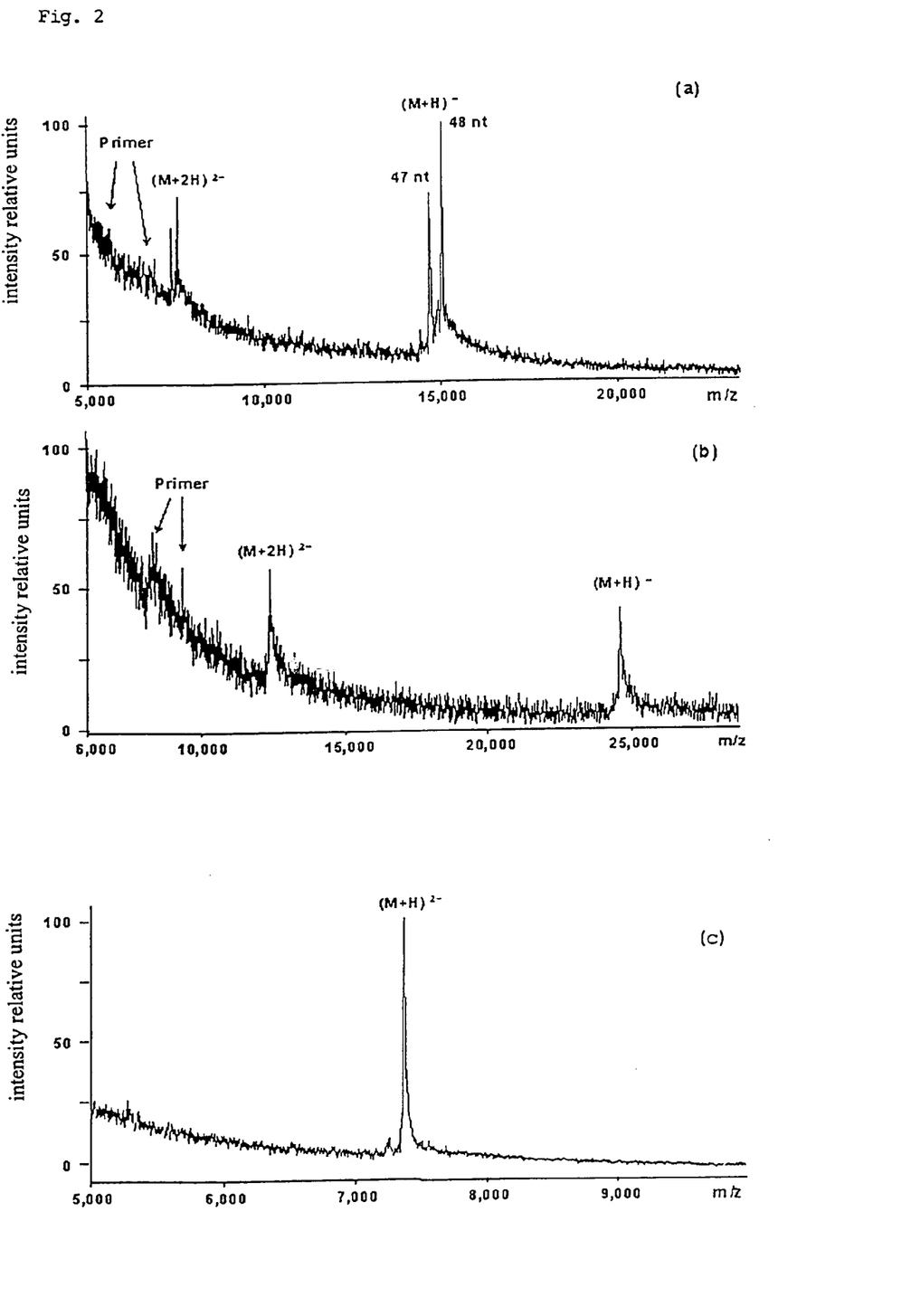
FIG. 2 (comprising FIGS. 2a, 2b and 2c) shows the isolation and purification of ssDNA and dsDNA by the method according to the invention for a MALDI-MS analysis.

In MALDI single-charged molecular ions of the species $(M+H)^+$ are preferably formed and double-charged molecular ions of the species $(M+2H)^{2+}$ are also formed at a lower frequency. If no special measures are employed PCR products are separated during the MALDI mass spectrometry and detected in the form of single strands. The signals of complementary single strands are often only partially resolved due to the small differences in mass. The size of the PCR products can nevertheless be determined by comparing the measured average masses with estimated values or values calculated on the basis of known sequences. The $(M+H)^+$ signals of non-separated primers would be registered in the spectra at the positions marked with arrows.

EXAMPLES

Example 1 dsDNA Isolation and Purification from PCR (Polymerase Chain Reaction)

Magnetic particles which have hydrophobic and hydrophilic groups on their surface are firstly washed three times with 150 µl EDTA solution (0.5 mol/l, pH 8) by magnetically separating the particles and discarding the supernatant. After the last wash the particles are taken up in EDTA solution and mixed. The mass concentration is 20 mg/ml.

The samples to be examined are placed in a microtitre plate (e.g. 96 well). 40 µl binding buffer (2.5 mol/l NaCl, 20% (w/w) PEG6000) and 10 µl of the particle suspension are added to 40 µl sample volume, mixed and incubated at room temperature for 10 min.

The microtitre plate containing the samples is subsequently placed for 2 min in a magnetic holder, the supernatant is discarded and the particles are washed twice with 150 µl washing buffer (40% ethanol) and subsequently dried in air for 2 to 5 min.

Finally the microtitre plate is removed from the magnetic holder and the particles are resuspended in 20 ml elution buffer (1 mmol/l Tris-HCl) and incubated for 5 min. The microtitre plate is then again placed in the magnetic holder and the eluate is removed after 2 min.

The DNA contained in the eluate could be used without further purification for concentration determinations, DNA sequencing etc.

Example 2 ds DNA Isolation and Purification from Cell Culture

Cells from an overnight culture were pelleted and the supernatant was discarded. The cell pellet was taken up in 40 µl resuspension buffer (50 mmol/l Tris-HCl, pH 8, 10 mmol/l EDTA, 100 µg/ml RNAse A) and mixed. Then 40 µl lysis buffer (200 mmol/l NaOH, 1% (w/w) SDS) was added and mixed. After adding 40 µl neutralization buffer (3 mol/l KOAc, pH 5.5) and mixing, it was centrifuged for 15 min at 13,000 rpm.

The supernatant was transferred to a fresh microtitre plate. Magnetic particles according to the invention were washed three times with 150 µl EDTA solution (0.5 mol/l pH 8) by magnetically separating the particles and discarding the supernatant. After the last wash the particles were taken up in EDTA solution and mixed. The mass concentration was 20 mg/ml.

120 µl binding buffer (2.5 mol/l NaCl, 20% (w/w) PEG6000) and 10 µl of the particle suspension was added to 120 µl sample volume. After mixing the preparation it was incubated for 5 min at room temperature.

The microtitre plate containing the samples was subsequently placed for 10 min in a magnetic holder, the supernatant was discarded and the particles were washed twice with 120 µl washing buffer (70% ethanol, 10 mmol/l Tris-HCl, pH 8, 1 mmol/l EDTA) and subsequently dried for 5 min in air.

The microtitre plate was then removed from the magnetic holder and the particles were resuspended in 50 µl elution buffer (1 mmol/l Tris-HCl, pH 8), incubated for 5 min and the plate was then again placed in the magnetic holder and the eluate was removed after 2 min.

The DNA contained in the eluate could be used without further purification for concentration determinations, DNA sequencing etc.

Example 3

Comparison of Yields

Figure 1A:
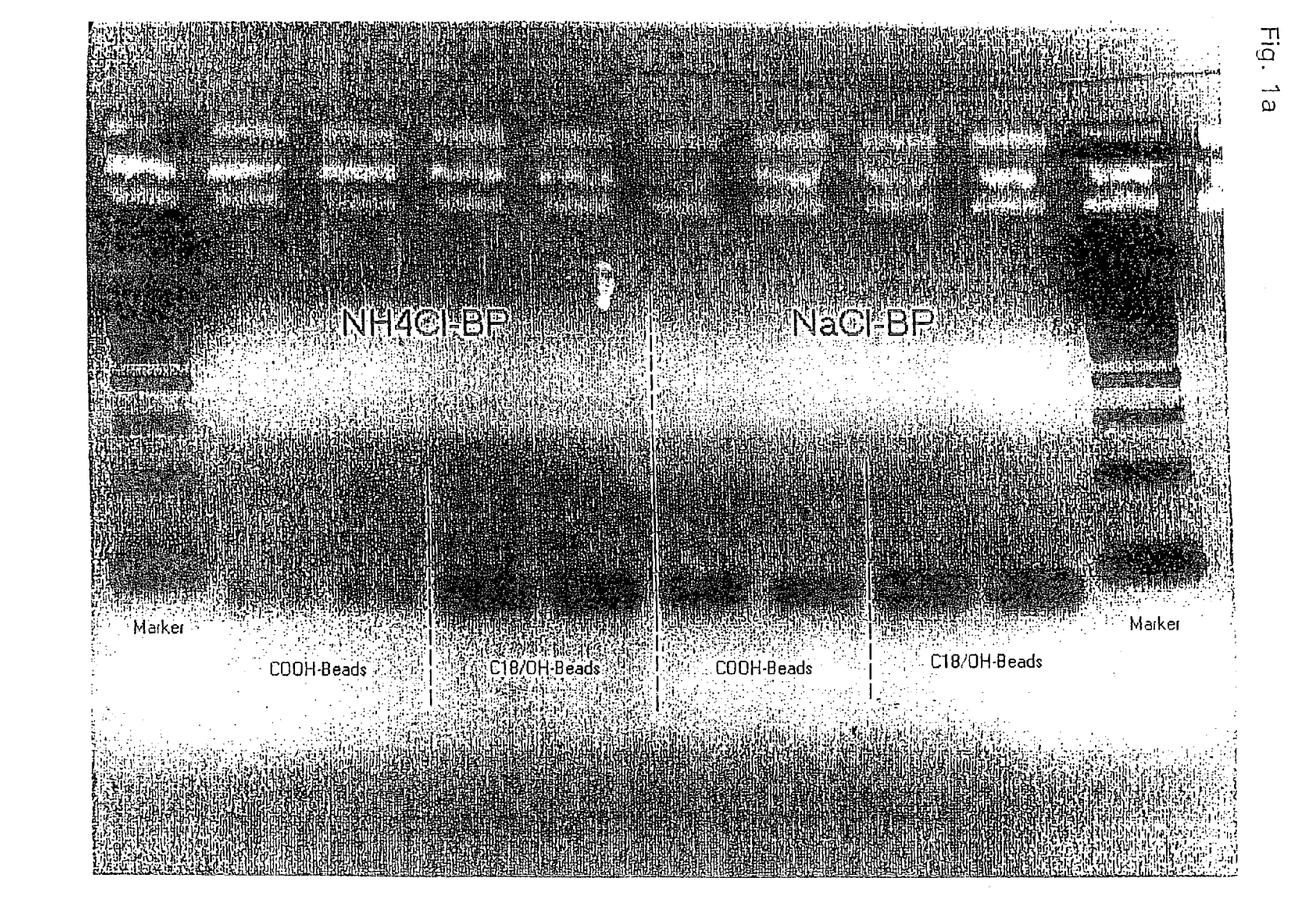
FIG. 1a shows a comparison of the yields using an $NH_4Cl$ binding buffer (left) and an NaCl binding buffer (right) for PCR products purified according to the invention (C18/OH beads) and for PCR products that have been purified using COOH-coated particles (COOH beads).
Figure 1B:
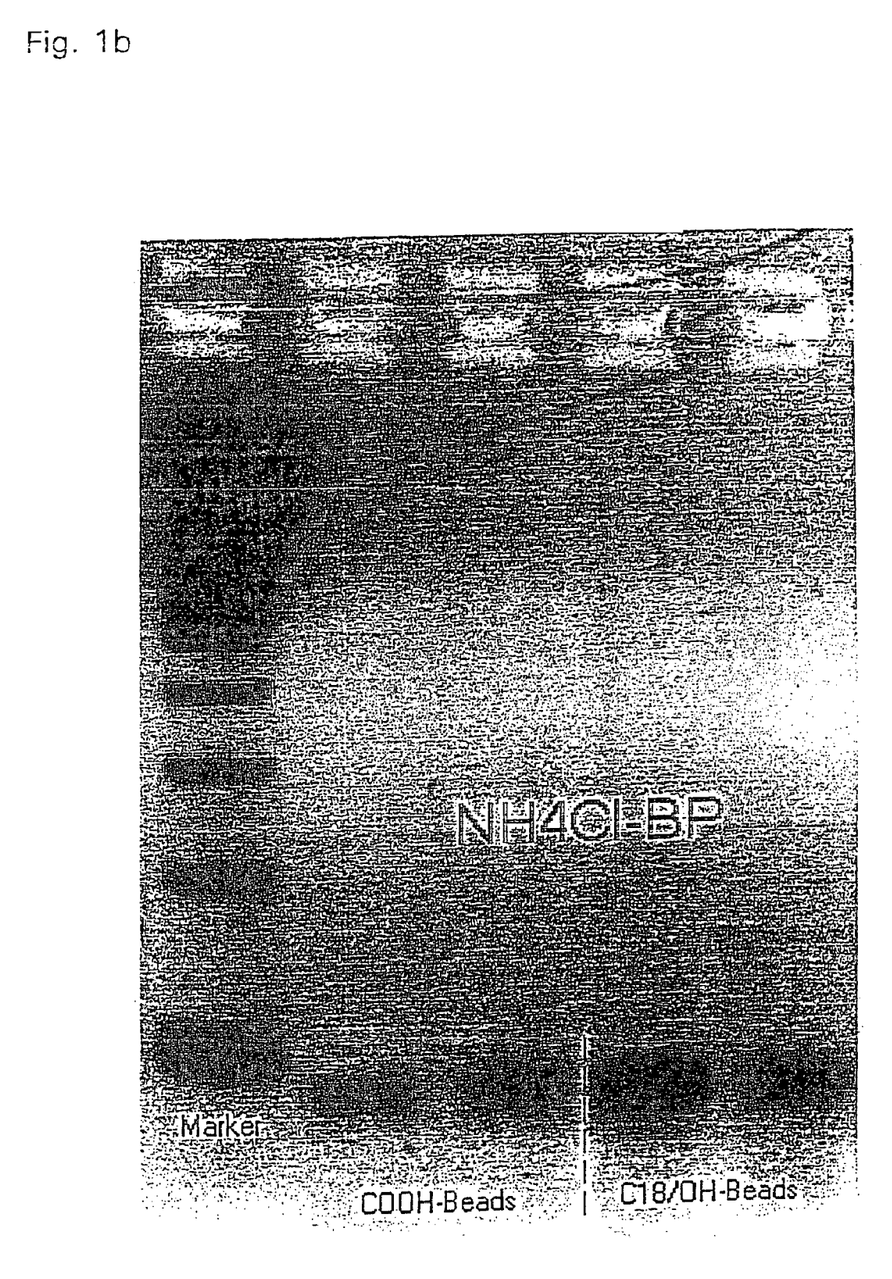
FIG. 1b shows a further comparison of yields using $NH_4Cl$ binding buffer.

FIG. 1 shows an agarose gel of purified 100 bp PCR products. The purification was carried out according to the invention and also using COOH-coated particles (cf. U.S. Pat. No. 5,705,628). 100 pmol of a ssDNA of 32 nucleotides in size was added to the PCR products before purification. As can be seen from the figure of the agarose gel, the desired nucleic acid is obtained in a purified form and undesired substances including the 32 nucleotide ssDNA are separated. Furthermore the yield of the method according to the invention is considerably higher than that of the COOH-coated particles.

Example 4

Purification Protocol

In order to purify double-stranded DNA (cf. FIGS. 2a and 2b) PCR reactions were each carried out in 40 µl reaction volumes in 96-well microtitre plates. Magnetic particles were magnetically separated before use, the supernatant was removed by pipette and the particles were resuspended in an aliquot of the binding buffer. After completion of the amplification reaction, 5 µl of the suspension of the magnetic particles was added to each reaction vessel, followed by 50 µl binding buffer and namely 1.5 M NH$_4$CL/40 mM MgCl$_2$ in 40% (w/w) PEG 6000/60% (w/w) H$_2$O for the PCR products of 47/48 bp (cf. FIG. 2a) and 2.5 M NH$_4$Cl in 30% (w/w) PEG 6000/70% (w/w) H$_2$O for the PCR product of 80 bp.

The resulting suspension was thoroughly mixed and allowed to stand for 10 min. Afterwards the particles were separated magnetically, the supernatant was removed by pipette and replaced by 105 µl 65% (vol/vol) ethanol/35% (vol/vol) H$_2$O (washing solution 1). The magnetic particles were moved twice through the washing solution by transferring the vessels. Subsequently the supernatant was successively replaced by 115, 125 and 135 µl 1.5 M ammonium acetate in 30% (vol/vol) H$_2$O, 70% (vol/vol) ethanol during which the particles were moved five times through the new washing solution 2. The supernatants were in each case discarded. Finally the particles were washed twice with 145 µl 80% (vol/vol) ethanol/20% (vol/vol) H$_2$O) (washing solution 3) during which the particles were each moved twice through the solution. After the last supernatant was removed by pipette, the particles were allowed to stand in air for 10 min in order to allow the remaining ethanol to evaporate. Subsequently the particles were resuspended in 5 µl 1 mM Tris-HCl, pH 7.5 (elution solution). After 10 min the particles were separated magnetically and 0.5 µl of the supernatant was transferred onto a freshly cleaned MALDI sample carrier and mixed there with 0.5 µl matrix solution (200 mM 3-hydroxypicolinic acid in 30% (vol/vol) acetonitrile/70% H$_2$O (vol/vol). After evaporating the solvent, the sample was analysed in a Bruker Reflex II MALDI time-of-flight mass spectrometer.

In order to purify the single-stranded DNA (cf. FIG. 2c), 10 pmol of a 24 nucleotide oligodeoxyribonucleotide in 40 µl PCR reaction solution was added first and 5 µl of the suspension of the magnetic particles (in binding buffer) was added followed by 50 µl binding buffer (1.5 M NH$_4$C/40 mM MgCl$_2$ in 35% (w/w) PEG 6000/30% (vol/vol) ethanol). The washing procedure differed from that described above in that the first wash was omitted and the washing solution 2 was replaced by 100 mM ammonium acetate in 30% (vol/vol) H$_2$O/70% (vol/vol) ethanol. The elution and subsequent analysis of the purified product was carried out as described above.

What is claimed is:

1. A method for binding nucleic acids to a solid phase comprising contacting a solution containing nucleic acids with a solid phase containing hydrophobic groups for binding nucleic acids and hydrophilic groups for avoiding agglomeration of said solid phase on its surface, wherein a salt and polyethylene glycol are present in said solution during binding of the nucleic acids to said solid phase and said nucleic acids are reversibly and sequence-unspecifically bound to the surface via said hydrophobic groups.

2. The method as claimed in claim 1, wherein said surface has alkyl or aryl groups as hydrophobic groups.

3. The method as claimed in claim 2, wherein the alkyl groups are selected from C$_8$ alkyl, C$_{18}$ alkyl and mixtures thereof.

4. The method as claimed in claim 1, wherein the surface has hydroxyl groups as hydrophilic groups.

5. The method as claimed in claim 1, wherein the solid phase is solid particles.

6. The method as claimed in claim 1, wherein the solid phase is magnetic.

7. The method as claimed in claim 1, wherein the salt is an alkali, alkaline earth or/and ammonium halide.

8. The method as claimed in claim 1, wherein said polyethylene glycol has an average molar mass of 1000 to 20000 g/mol.

9. The method as claimed in claim 1, wherein the salt is at a concentration of 5 mmol/l to 4 mol/l.

10. The method as claimed in claim 1, wherein said polyethylene glycol is at a concentration of 5% by weight to 40% by weight.

11. The method as claimed in claim 1, wherein the nucleic acids are DNA.

12. The method as claimed in claim 1, wherein the nucleic acids are amplification products.

13. The method as claimed in claim 1, wherein single-stranded or double-stranded nucleic acids are selectively bound.

14. The method as claimed in claim 1, wherein the nucleic acid is selectively bound with regard to size in a range of $\geq 5$ nucleotides to $\leq 1000$ nucleotides.

15. A method for isolating or/and purifying nucleic acids comprising
    (a) providing a solution containing nucleic acids,
    (b) contacting the solution containing nucleic acids with a solid phase which has hydrophobic and hydrophilic groups on its surface, wherein a salt and polyethylene glycol are present in said solution during binding of the nucleic acids via said hydrophobic groups to said solid phase and the nucleic acid is reversibly and sequence-unspecifically bound to the surface of the solid phase, and
    (c) separating the solid phase from the solution.

16. The method according to claim 15, wherein said nucleic acid is detached from the solid phase.

17. The method as claimed in claim 15, wherein the solid phase is magnetic and the solid phase is separated from the solution by magnetic means.

18. The method as claimed in claim 15, wherein the solid phase separated in step (c) is washed with a buffer solution which detaches impurities bound to the solid phase but not the nucleic acids bound to the solid phase.

19. The method as claimed in claim 16, wherein the nucleic acid is detached by means of an elution solution.

20. The method as claimed in claim 16, wherein the nucleic acid detached from the solid phase and the solid phase are separated by magnetic means.

21. The method as claimed in claim 16, further comprising subjecting the nucleic acid obtained to a mass spectrometric analysis.

22. A method for determining a nucleotide sequence comprising
    (a) binding a nucleic acid strand to a solid phase according to the method of claim 1, and
    (b) sequencing the nucleic acid strand by known methods.

23. The method as claimed in claim 22, further comprising (c) purifying the sequencing products.

24. A method for extending nucleic acids comprising the steps
    (a) binding a nucleic acid to a solid phase according to the method of claim 1, and
    (b) extending the nucleic acid by at least one nucleotide by known methods.

25. A method for detecting an analyte in a sample, comprising contacting a solution containing nucleic acids with a solid phase, wherein said solid phase has hydrophobic and hydrophilic groups on the surface, and wherein a salt and polyethylene glycol are present in said solution during binding of the nucleic acids to said solid phase and the nucleic acids are reversibly and sequence-unspecifically bound to the surface of said solid phase via said hydrophobic groups, subsequently contacting the solid phase with a sample, and detecting any analyte by means of the binding to the bound nucleic acids.

26. A reagent kit for carrying out a method as claimed in claim 1 comprising:

(a) a binding buffer which contains a salt and a polyethylene glycol, and (b) a solid phase which has on its surface hydrophobic groups which bind nucleic acids and hydrophilic groups which prevent agglomeration.

27. The reagent kit as claimed in claim 26, further comprising, (c) an elution buffer that can be used to detach the nucleic acid bound to this surface, and (d) a washing buffer which can be used to separate impurities bound to the solid phase.

\* \* \* \* \*

UNITED STATES PATENT AND TRADEMARK OFFICE
CERTIFICATE OF CORRECTION

PATENT NO. : 7,022,835 B1
APPLICATION NO. : 10/069974
DATED : April 4, 2006
INVENTOR(S) : Rauth et al.

It is certified that error appears in the above-identified patent and that said Letters Patent is hereby corrected as shown below:

Line 75 (Inventors): The last inventors name is misspelled.

The correct spelling is Eckhard NORDHOFF

Signed and Sealed this

Fifth Day of September, 2006

JON W. DUDAS
*Director of the United States Patent and Trademark Office*